(12) United States Patent
Quijano et al.

(10) Patent No.: US 7,022,134 B1
(45) Date of Patent: Apr. 4, 2006

(54) BIFURCATED BIOLOGICAL PULMONARY VALVED CONDUIT

(75) Inventors: Rodolfo C. Quijano, Laguna Hills, CA (US); Robert Loya, Fontana, CA (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/605,118

(22) Filed: Jun. 28, 2000

Related U.S. Application Data

(63) Continuation of application No. 09/252,333, filed on Feb. 18, 1999, now Pat. No. 6,110,201.

(51) Int. Cl.
*A61F 2/06* (2006.01)

(52) U.S. Cl. ............... 623/1.24; 623/1.35; 623/1.31

(58) Field of Classification Search ............... 623/1.24, 623/1.1, 1.35, 1.3, 1.31; 600/36; 606/8, 606/153
See application file for complete search history.

(56) References Cited

U.S. PATENT DOCUMENTS

| 15,192 | A | * | 6/1856 | Peale ..................... 623/1.24 |
| 2,127,903 | A | | 8/1938 | Bowen |
| 3,805,793 | A | | 4/1974 | Wright |
| 4,350,492 | A | | 9/1982 | Wright et al. |
| 4,728,328 | A | | 3/1988 | Hughes et al. |
| 5,078,735 | A | * | 1/1992 | Mobin-Uddin ............ 128/898 |
| 5,156,619 | A | * | 10/1992 | Ehrenfeld ................ 623/1.31 |
| 5,197,976 | A | * | 3/1993 | Herweck et al. .......... 623/1.27 |
| 5,236,447 | A | | 8/1993 | Kubo et al. |
| 5,500,014 | A | * | 3/1996 | Quijano et al. ........... 623/1.24 |
| 5,609,626 | A | | 3/1997 | Quijano et al. |
| 5,755,734 | A | * | 5/1998 | Richter et al. ............ 128/898 |
| 5,797,930 | A | | 8/1998 | Ovil |
| 5,989,287 | A | * | 11/1999 | Yang et al. .............. 623/1.36 |
| 6,110,201 | A | * | 8/2000 | Quijano et al. ........... 623/2.1 |

OTHER PUBLICATIONS

Vascular Surgery—Principles and Practice; Chapter 61—"Venous Reconstructive Surgery"; PP 758-767; Arthur: Luis A. Queral.
"Repairs of Venous Valves Using Silicone Cuffs"; Author: Rodney J. Lane; PP 410-417.
Valvular Obstruction of Blood Flow Through Saphenous Veins; Authors: Daniel B. Walsh, M.D., et al.; PP 39-42.

* cited by examiner

*Primary Examiner*—Brian E. Pellegrino
(74) *Attorney, Agent, or Firm*—Tom Berry; Jeff Hohenshell

(57) ABSTRACT

The present invention comprises a pulmonary valved conduit that permits inflow diameters greater than about 22 mm while still maintaining the advantages of a naturally-formed biological valved conduit. Specifically, the present invention comprises a valved vascular prosthetic having an inflow conduit comprising a manifold formed from the sealed attachment of at least two venous valvular conduits.

42 Claims, 3 Drawing Sheets

BIFURCATED BIOLOGICAL PULMONARY VALVED CONDUIT

This is a continuation of U.S. patent application Ser. No. 09/252,333, filed Feb. 18, 1999, now U.S. Pat. No. 6,110,201.

BACKGROUND OF THE INVENTION

Pulmonary valved conduits, used to replace diseased arteries such as the pulmonary artery, have been used for the last thirty years. These pulmonary valved conduits have been generally effective at treating pulmonary atresia, pulmonary stenosis, or pulmonary insufficiency. In early embodiments, the conduits consisted of crimped woven or knit polyester tubes housing a valve fabricated from metal components or metal/plastic polymer components. Later valves consisted of metal frames suspending ceramic flat or curved (convex or concave) discs or hemidiscs that were passive to the flow of blood exiting the chambers of the heart.

There were at least two disadvantages of these pulmonary valved conduits. First, there was a need to preclot the polyester tubes in order to preclude blood from seeping through the pores of the knit or woven material. Second, after months of usage, a layer of fibrinous material formed in the inner lumen over time from the accumulation of blood proteins. This layer of fibrinous material, referred to as "intimal peel," often separated from the inner wall and interfered with the effective operation of the valve. An ineffective valve required re-operation to replace the conduit and valve, if caught in time. In some instances, if valve replacement came too late, the results were fatal.

In the case of a mechanical valve made of metals and ceramics, there was also the need to continuously medicate the patient with anticoagulants for the duration of his life. That is because no man-made material that is impervious to the clotting effects of blood exists today. Anticoagulation of the patient prevents coagulation of blood on the surfaces of the inner lumen and on the sinuses of the cusps of the valves. Moreover, for children suffering from congenital pulmonary atresia or pulmonary insufficiency, the use of pulmonary valved conduits were not always effective. As the child grew, the prosthetic was less effective due to its inadequate size, requiring frequent replacement. Also, for children especially, anticoagulation requirements are difficult to regiment.

Beginning in the early 1970s, biological valves were used within the crimped polyester conduits to produce a hybrid prosthetic referred to as a biological valved conduit. It was believed that a biological valve, such as a porcine aortic valve fixed with formaldehyde or glutaraldehyde, would eliminate the need for lifetime anticoagulation administration. While the desired result was achieved, there was still the problem of separation of the "intimal peel" from the inner lumen. The intimal peel clogged the leaflets of the biological valve. Moreover, while a porcine aortic valve functioned relatively well as a replacement aortic valve, where the blood pressures from the left ventricle are substantially high (80–120 mmHg), it did not function nearly as effective as a replacement pulmonary valve, where the blood pressures from the right ventricle are quite low (0–15 mmHg). The porcine aortic valve leaflets, which are relatively thick, become substantially less flexible when "fixed" by chemical solutions. Opening at low pressures becomes more difficult. Also, the flow therethrough becomes turbulent, which undesirably promotes the degeneration of the biological material.

The disadvantages mentioned above can be minimized or overcome by using a naturally formed biological conduit which integrates a valve suitable for pulmonary replacement. Preferably, the valve opens and remains open with minimal resistance to the flow of blood at relatively low pressures of less than 1 mm Hg. The valve should also preferably close under the effect of minimal backflow of blood and be capable of withstanding backflow pressures of up to 200–300 mm Hg. An example of a naturally-formed valvular conduit is described in U.S. Pat. No. 5,500,014 to Quijano, et al., the entire specification of which is incorporated herein by reference.

Even this arrangement is limited in that the naturally formed donor conduits have normally minimum diameters of about 22 mm. The largest naturally occurring biological valved conduits are veins with venous valves found in the jugular veins of caprine, cervine, canine, ovine, bovine, equine and other quadruped species and marsupials (e.g., kangaroos and wallabies). While children may be treated effectively with pulmonary valved conduits having such diameters of 22 mm or less, many adolescents and adults require larger-diameter prosthetics. The flow capacity of a pulmonary conduit exiting the right ventricle must be large enough to permit oxygenation of the blood at a sufficient rate to maintain systemic perfusion with blood returning to the heart from the lungs. With normal pulmonary circulation, the blood exiting the right heart through the pulmonary artery (trunk) divides into two separate flows: the right pulmonary artery servicing the right lung, and the left pulmonary artery servicing the left lung. That requires that each lung receive enough flow of blood through each of the two pulmonary arteries emanating from the pulmonary trunk. That flow capacity often requires a diameter greater than the 22 mm found in the jugular veins of donor animals.

SUMMARY OF THE INVENTION

The present invention comprises a pulmonary valved conduit that permits inflow diameters greater than about 22 mm while still maintaining the advantages of a naturally-formed biological valved conduit. Specifically, the present invention comprises a vascular prosthetic suitable for replacing a patient's damaged or missing pulmonary valve, said prosthetic comprising an inflow conduit comprising a manifold formed from the sealed attachment of a plurality of donor valved blood vessels, each of said blood vessels housing a biological valve integral therewith, said blood vessels configured to permit the flow of blood therethrough by the valve opening at a relatively low pressure and configured to prevent the backflow of blood therethrough by the valve closing so as to withstand relatively high pressures, said manifold formed upstream of each of the biological valves so as not to interfere with the effective operation of the biological valves, said inflow conduit having a resulting flow capacity following sealed attachment that is larger than the original flow capacity of each of the donor blood vessels, said prosthetic also comprising an outflow conduit positioned downstream of each of the biological valves.

The present invention prosthetic is prepared by using two approximately equal sized (diameter) jugular valved veins obtained from one of the quadrupeds identified above and attaching them in such a fashion to provide a resulting inflow area larger than each of the original donor veins. The inventive manifold does not alter or disturb the configuration of the valve itself. In the preferred embodiment, a bifurcated device is created wherein each of the branches includes its own biological valve flow. Various means of attachment can be used, such as stitching with medical surgical suture, or by means of protein sealants, glues, collages or laser radiation beams. Moreover, the attachment is preferably made so as to minimize the angle of transition of the blood running through the conduit at the site of the bifurcation.

DETAILED DESCRIPTION OF THE PREFERRED EMBODIMENT

Figure 1:
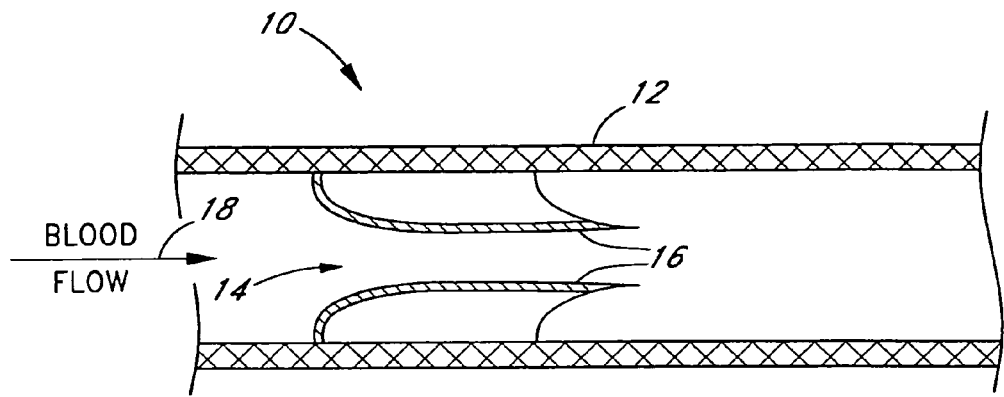
FIG. 1 is a cross-section of a venous valvular conduit, showing the valve leaflets in an open position.

With reference to FIG. 1, the present invention improves upon the use of a naturally-formed venous valvular conduit 10 consisting of a blood vessel 12 housing a biological valve 14. The valve 14 consists of a plurality of leaflets 16 (two shown) that easily open upon the flow of low pressure blood 18, but closely tightly against a relatively low backpressure of blood; remaining sealed even against backpressures as high as 200–300 mmHg. Such venous valvular conduits may be found, as indicated above, in one of many quadrupeds. Preferably, the donor venous valvular conduit is a section of the jugular vein of a quadruped, the diameters of which approach about 22 mm. While humans have naturally-formed venous valvular conduits, none approach that diameter.

Figure 2:
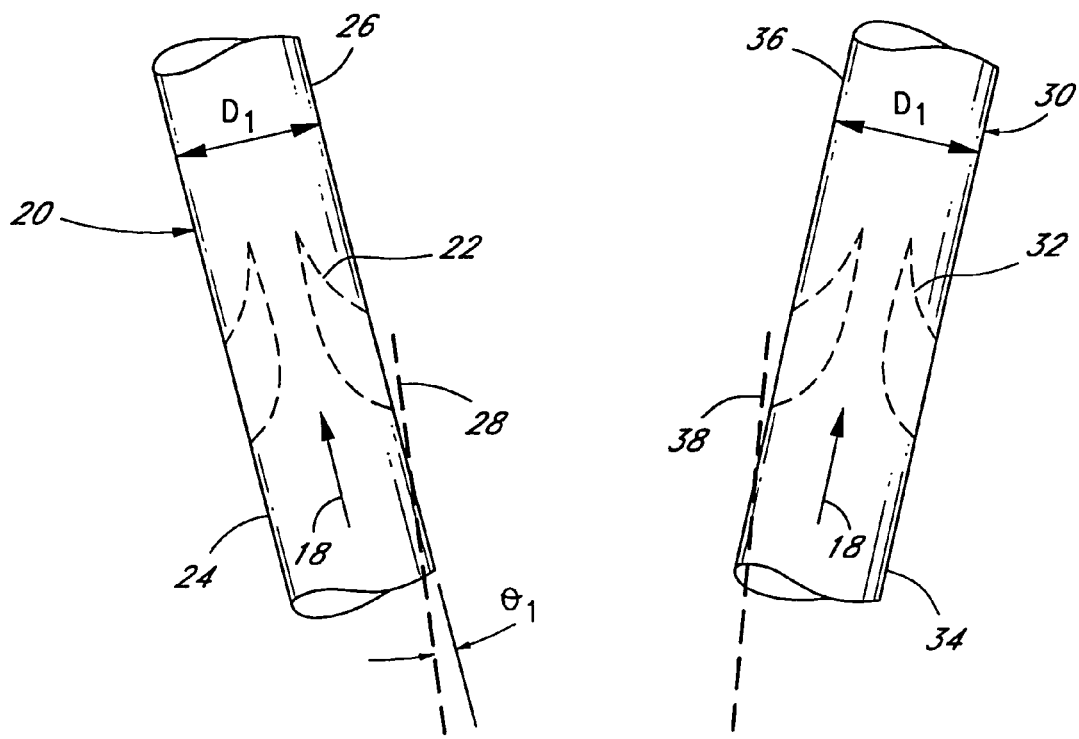
FIG. 2 is a perspective of two section of venous valvular conduits, indicating where a proposed slicing of the conduits is to be made.
Figure 3:
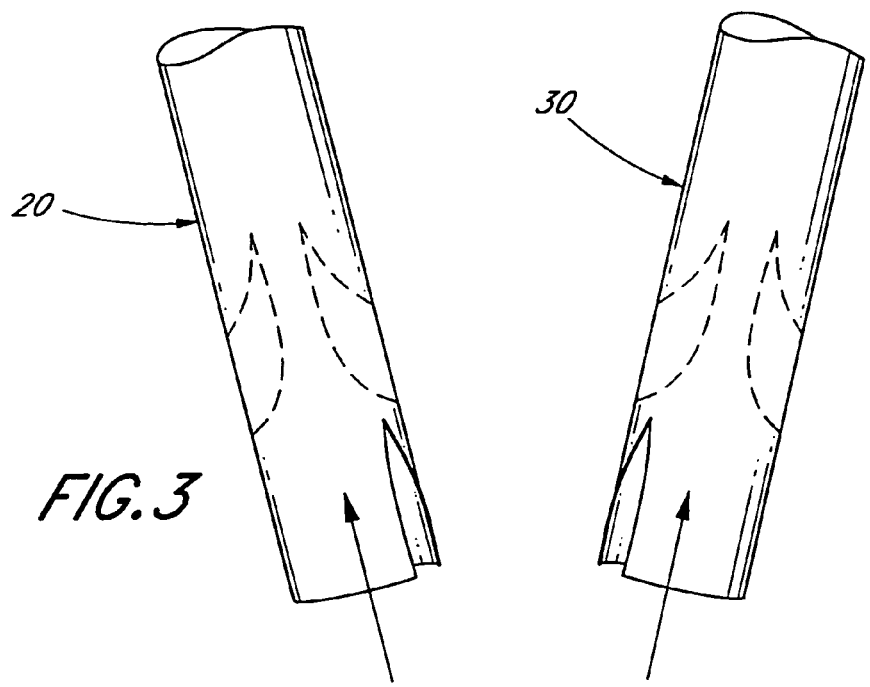
FIG. 3 is a perspective of the two section of venous valvular conduits of FIG. 2, indicating where the slices of the conduits have been made in preparation for attachment.
Figure 4:
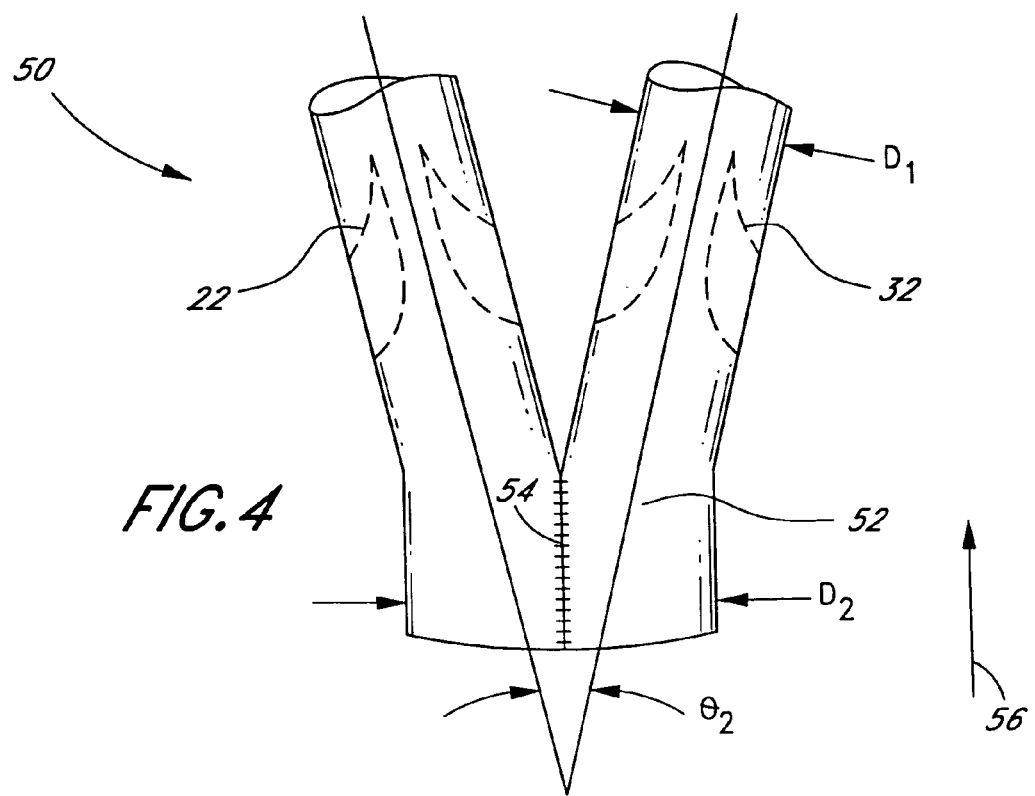
FIG. 4 is a perspective view of the preferred embodiment of the present invention showing how the two venous valved conduits of FIG. 2 have been joined.

With reference to FIGS. 2–4, the present invention comprises a method of making a vascular prosthetic comprising a valvular conduit suitable for pulmonary valve replacement, wherein the conduit has a diameter greater than 22 mm. The flow output of many human adult right ventricles requires that a pulmonary valve prosthetic have diameters greater than 22 mm to maximize the effectiveness of the prosthetic.

With specific reference to FIG. 2, the present invention maximizes that benefit by inventively combining two generally-equally-sized donor valvular conduits 20, 30, each having a biological valve 22, 32 housed therewithin. Each conduit 20, 30 has an inflow end 24, 34 and an outflow end 26, 36. The donor valvular conduits are preferably fixed to effectively preserve the conduits in an aldehyde solution; preferably glutaraldehyde, or any other similar solution such as formaldehyde. That entails, for example, soaking the tissue in the aldehyde solution or passing the solution through the valved conduit while immersing the conduit in said solution. Other types of fixation include gamma radiation and polyepoxy compounds. In the preferred embodiment, a slice of the conduits 20, 30 is made where indicated at 28, 38.

Referring to FIG. 3, the slicing of each conduit 20, 30 results in an angular sectioned inflow end 24, 34 configured to be joined in a manner shown in FIG. 4. As shown in FIG. 4, the resulting vascular prosthetic 50 comprises an inflow end manifold 52 having a diameter D2. Where the diameter of each donor conduit is D1, the diameter D2 of the resulting prosthetic conduit inflow end manifold 52 is greater than D1. Where it is desired to have a vascular prosthetic with an inflow end diameter greater than 22 mm, the preferred embodiment of the present method comprises attaching two donor valvular conduits having diameters substantially less than about 22 mm in the manner shown in FIGS. 2 and 3. The resulting diameter D2 will be greater than 22 mm.

As shown in FIG. 4, the present invention prosthetic 50 comprises the inflow end manifold 52 having a seam 54 upstream of the two donor biological valves 22, 32. Preferably, to minimize the angle of transition for the blood flow 56, the slice cut from the two donor conduits 20, 30 is made at an angle ($\theta1$) of less than about 15°, although other angles may be appropriate. The resulting angle ($\theta2$) of the vascular prosthetic is, therefore, preferably less than 30°, although other angles may be appropriate. Where desired, the resulting prosthetic itself may be preserved via chemical fixation or other type of fixation.

It is contemplated that the attachment of sectioned donor conduits 20, 30 be made via a plurality of stitches made in one or more passes. Preferably, a single pass of stitches is made on the interior to maintain as smooth an inner lumen as possible. Furthermore, it is preferable that each stitch be applied in a manner that said stitches will not unravel when tissue and included neighboring stitches are severed. Discrete stitches may be used. Externally, at least one pass, but preferably two passes, of stitches is applied to reinforce the attachment. Other methods of attachment are also contemplated, including biological and chemical sealants, and laser beam radiation.

With the embodiment of FIG. 4, the inflow end 52 may be attached directly to the right ventricle at our about the location of the inflow to the patient's pulmonary trunk. Each outflow end 26, 36 of the prosthetic may be attached to the left and right pulmonary arteries, respectively, thereby bypassing the patient's diseased or missing pulmonary valve. Alternatively, each outflow end 26, 36 could be attached to different locations of the downstream end of the patient's pulmonary trunk, if desired.

Figure 5:
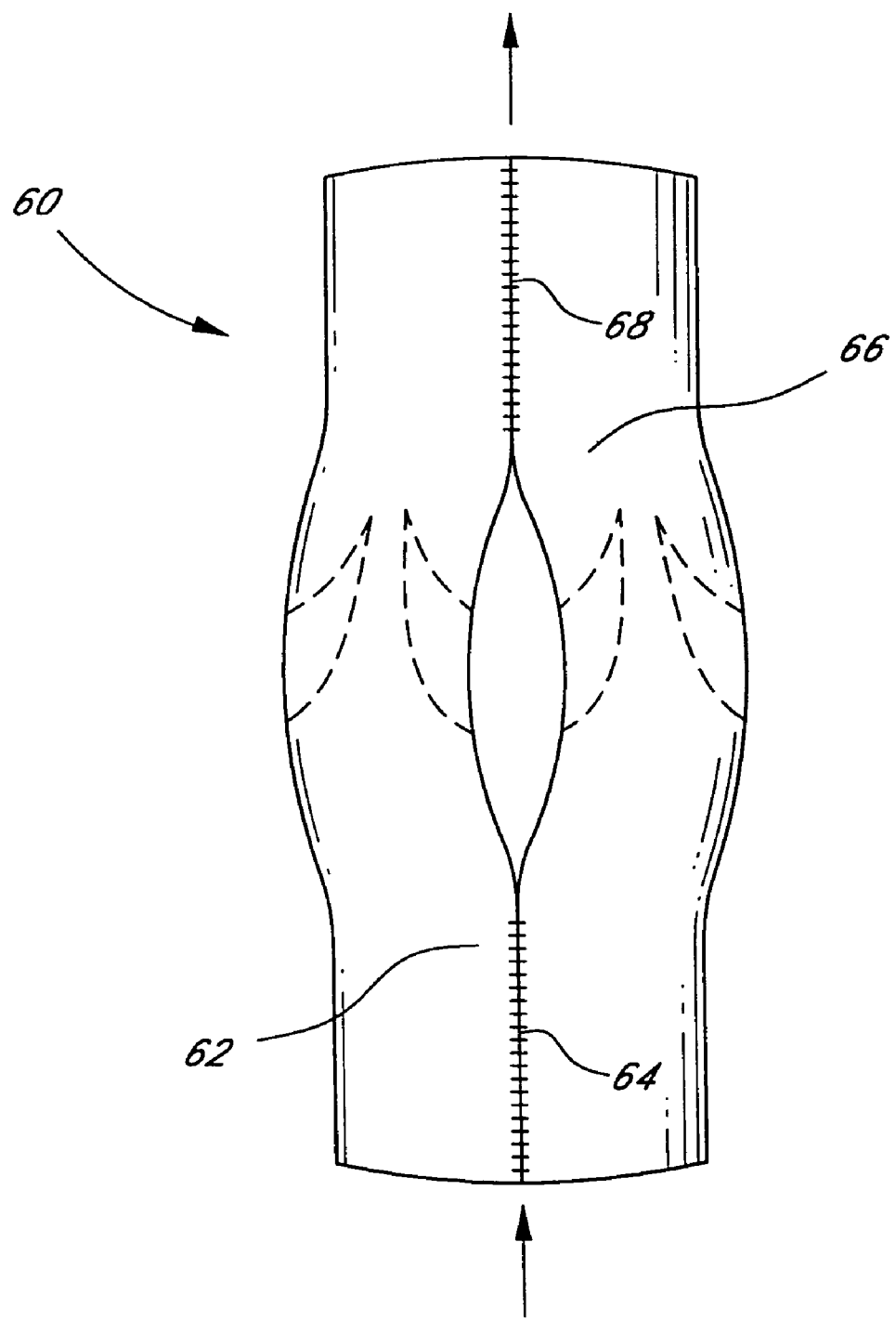
FIG. 5 is a perspective view of a variation of the embodiment of FIG. 4 showing a unitary outflow end.

With reference to FIG. 5, a second embodiment 60 of the present invention is contemplated. The second embodiment 60 comprises an inflow end manifold 62 having a seam 64 and an outflow end manifold 66 having a second seam 68. Where it is desired to have a prosthetic with a single outflow end, the present inventive method further comprises slicing the outflow ends of two donor valvular conduits in the same or similar manner as described above and shown in FIG. 3. Performing those steps, the outflow ends of the donor valvular conduits may be attached to form the second outflow end manifold 66 wherein the resulting seam 68 is formed from a plurality of passes of stitches, as described above. This second embodiment 60 may be attached at the inflow end to the right ventricle and at the outflow end to the pulmonary trunk, thereby bypassing the patient's diseased or missing pulmonary valve.

What is claimed is:

1. A vascular prosthetic comprising:
   at least two chemically fixed biological tissue valvular conduits, each of said conduits having an angular sectioned inflow end and an outflow end and a valve of chemically fixed biological tissue housed therein;
   an inflow conduit having a large diameter cross-sectional area and a smooth inner lumen;
   a seam, the seam comprising a plurality of single pass stitches, the seam on the angular sectioned inflow ends to attach the inflow ends to each other to define the inflow conduit, the smooth inner lumen oriented at an angle of less than 30 degrees to each of the at least two valvular conduit outflow ends, the inflow conduit positioned upstream of each of said valves.

2. The vascular prosthetic of claim 1 wherein the inflow conduit is suitable for attachment to a heart to receive blood from the right ventricle.

3. The vascular prosthetic of claim 1 wherein-at least one outflow end is suitable for attachment to a pulmonary trunk.

4. The vascular prosthetic of claim 1 wherein the outflow ends are suitable for attachment to first and second pulmonary arteries.

5. The vascular prosthetic of claim 1 wherein the valve of each valvular conduit opens at pressures as low as about 1 mm Hg and remains sealably closed so as to withstand backflow pressures greater than about 200 mm Hg.

6. The vascular prosthetic of claim 1 wherein the cross-sectional area of the inflow end of the vascular prosthetic is greater than about 22 mm.

7. The vascular prosthetic of claim 1 wherein the cross-sectional area of the inflow end of the prosthetic is greater than about 28 mm.

8. The vascular prosthetic of claim 1 wherein the fixed tissue conduits are fixed by an aldehyde.

9. The vascular prosthetic of claim 1 wherein the fixed tissue conduits are fixed by a polyepoxy compound.

10. A vascular prosthetic comprising:
a "Y" shaped conduit of fixed biological tissue having a large diameter inflow conduit, a bifurcated outflow conduit comprising two valvular conduit outflow ends and an integral valve disposed in each valvular conduit outflow ends, the pulmonary valved conduit formed from chemically fixed biological tissue, wherein each of said valvular conduits ends is joined at a seam forming the inflow conduit, the seam including a plurality of stitches forming a smooth inner lumen along the large diameter inflow conduit, the smooth inner lumen in fluid communication across the integral valves with the flow path in the valvular conduit outflow ends at an angle of –transition less than 15 degrees from said inflow conduit to either of the valvular conduit outflow ends, the large diameter inflow conduit with a cross-sectional area larger than the cross-sectional area of either of the two valvular conduit outflow ends forming the "Y" shape.

11. The vascular prosthetic of claim 10 wherein the single inflow end is suitable for attachment to a heart to receive blood from the right ventricle.

12. The vascular prosthetic of claim 10 wherein the valvular conduits comprise first and second outflow ends, wherein at least one outflow end is suitable for attachment to a pulmonary trunk.

13. The vascular prosthetic of claim 12 wherein the first and second outflow ends are suitable for attachment to first and second pulmonary arteries.

14. The vascular prosthetic of claim 10 wherein the valve of each valvular conduit opens at pressures as low as about 1 mm Hg and remains sealably closed so as to withstand backflow pressures greater than about 200 mm Hg.

15. The vascular prosthetic of claim 10 wherein the cross-sectional area of the inflow end of the vascular prosthetic is greater than about 22 mm.

16. The vascular prosthetic of claim 10 wherein the cross-sectional area of the inflow end of the vascular prosthetic is greater than about 28 mm.

17. The vascular prosthetic of claim 10 wherein the stitches are formed in a single pass.

18. The vascular prosthetic of claim 10 wherein the fixed tissue conduits are fixed by an aldehyde.

19. The vascular prosthetic of claim 10 wherein the fixed tissue conduits are fixed by a polyepoxy compound.

20. A vascular prosthetic comprising:
an inflow conduit comprising a manifold formed from the attachment of two donor valved blood vessels, the attachment including a plurality of stitches forming a smooth inner lumen, each of said two blood vessels housing a biological valve integral therewith, each blood vessel configured to permit the flow of blood therethrough by the valve opening at a relatively low pressure and configured to prevent the backflow of blood therethrough by the valve closing so as to withstand relatively high pressures, said manifold formed at an angle of transition of the blood flow therethrough that is less than 30 degrees upstream of the biological valves so as not to interfere with the effective operation of the biological valves, the inflow conduit with a cross-sectional area larger than the cross-sectional area of either of the inflow ends of each of the donor blood vessels, and an outflow conduit positioned downstream of each of the biological valves.

21. The vascular prosthetic of claim 20 wherein the inflow conduit is suitable for attachment to a heart to receive blood from the right ventricle.

22. The vascular prosthetic of claim 20 wherein the donor blood vessels comprise first and second outflow ends, wherein at least one outflow end suitable for attachment to a pulmonary trunk.

23. The vascular prosthetic of claim 22 wherein the first and second outflow ends are suitable for attachment to first and second pulmonary arteries.

24. The vascular prosthetic of claim 20 wherein the valve of each donor blood vessel opens at pressures as low as about 1 mm Hg and remains sealably closed so as to withstand backflow pressures greater than about 200 mm Hg.

25. The vascular prosthetic of claim 20 wherein the cross-sectional area of the inflow conduit of the vascular prosthetic is greater than about 22 mm.

26. The vascular prosthetic of claim 20 wherein the cross-sectional area of the inflow conduit of the vascular prosthetic is greater than about 28 mm.

27. The vascular prosthetic of claim 20 wherein the plurality of donor blood vessels are chemically fixed biological tissue.

28. The vascular prosthetic of claim 27 wherein the plurality of donor blood vessels are fixed by an aldehyde.

29. The vascular prosthetic of claim 20 wherein the stitches are formed in a single pass.

30. The vascular prosthetic of claim 27 wherein the plurality of donor blood vessels are fixed by a polyepoxy compound.

31. The prosthetic of claim 20 wherein the plurality of donor blood vessels each comprise a vein segment.

32. The prosthetic of claim 31 wherein the plurality of donor blood vessels each comprise the jugular vein of a donor quadruped or marsupial.

33. The prosthetic of claim 32 wherein the valved blood vessels each comprise the jugular vein of a donor caprine, cervine, canine, ovine, bovine, equine or marsupial.

34. A vascular prosthetic comprising:
two chemically fixed biological tissue valvular conduits, each of said conduits having an angular sectioned inflow end and an outflow end and a valve of chemically fixed biological tissue housed therein, each of said conduits comprising the jugular vein of a donor quadruped or marsupial;
wherein each of said conduits is joined at the angular sectioned inflow ends by stitches to form a single inflow end having a smooth inner lumen with a single inflow end cross-sectional area larger than the cross-sectional area of any of the inflow ends of said valvular conduits, the joinder providing an angle of transition of the blood flow through the single inflow end and into the outflow ends that is less than 30 degrees.

35. The vascular prosthetic of claim 34 wherein the single inflow end is suitable for attachment to a heart to receive blood from the right ventricle.

36. The vascular prosthetic of claim 34 wherein the valvular conduits comprise first and second outflow ends, wherein at least one outflow end is suitable for attachment to a pulmonary trunk.

37. The vascular prosthetic of claim 34 wherein the valvular conduits comprise first and second outflow ends that are suitable for attachment to first and second pulmonary arteries.

38. The vascular prosthetic of claim 34 wherein the valve of each valvular conduit opens at pressures as low as about 1 mm Hg and remains sealably closed so as to withstand backflow pressures greater than about 200 mm Hg.

39. The vascular prosthetic of claim 34 wherein the cross-sectional area of the inflow end of the vascular prosthetic is greater than about 22 mm.

40. The vascular prosthetic of claim 34 wherein the cross-sectional area of the inflow end of the vascular prosthetic is greater than about 28 mm.

41. The vascular prosthetic of claim 34 wherein the fixed tissue conduits are fixed by an aldehyde.

42. The vascular prosthetic of claim 34 wherein the fixed tissue conduits are fixed by a polyepoxy compound.

* * * * *